(12) United States Patent
Hamel et al.

(10) Patent No.: US 11,872,376 B2
(45) Date of Patent: Jan. 16, 2024

(54) INJECTION DEVICE

(71) Applicant: Duoject Medical Systems Inc., Bromont (CA)

(72) Inventors: Simon Hamel, Knowlton (CA); Andrea Chagnon, Bromont (CA); Sylvain Cloutier, Orford (CA)

(73) Assignee: DUOJECT MEDICAL SYSTEMS INC., Bromont (CA)

( * ) Notice: Subject to any disclaimer, the term of this patent is extended or adjusted under 35 U.S.C. 154(b) by 3 days.

(21) Appl. No.: 16/602,881

(22) PCT Filed: Jun. 19, 2018

(86) PCT No.: PCT/CA2018/000124
§ 371 (c)(1),
(2) Date: Dec. 16, 2019

(87) PCT Pub. No.: WO2018/232489
PCT Pub. Date: Dec. 27, 2018

(65) Prior Publication Data
US 2021/0138155 A1 May 13, 2021

(30) Foreign Application Priority Data
Jun. 19, 2017 (CA) .................................. CA 2971263

(51) Int. Cl.
| A61M 5/24 | (2006.01) |
| A61M 5/32 | (2006.01) |
| A61M 5/50 | (2006.01) |
| A61M 5/315 | (2006.01) |

(52) U.S. Cl.
CPC ...... *A61M 5/2422* (2013.01); *A61M 5/31501* (2013.01); *A61M 5/3293* (2013.01); *A61M 5/50* (2013.01)

(58) Field of Classification Search
CPC .. A61M 5/2422; A61M 5/315; A61M 5/3293; A61M 2202/06; A61M 5/31501; A61M 5/3205; A61M 5/321; A61M 5/322; A61M 5/3221; A61M 5/3232;
(Continued)

(56) References Cited

U.S. PATENT DOCUMENTS

| 2001/0037090 A1* | 11/2001 | Cherif-Cheikh | .... A61M 5/3257 604/198 |
| 2002/0169421 A1* | 11/2002 | McWethy | ........... A61M 5/3271 604/192 |
| 2015/0238706 A1* | 8/2015 | Reynolds | ............ A61M 5/3298 604/88 |

* cited by examiner

*Primary Examiner* — Shefali D Patel
(74) *Attorney, Agent, or Firm* — MEDLER FERRO WOODHOUSE & MILLS PLLC

(57) ABSTRACT

An injection device for injecting, the injection device comprising a housing having an interiorly facing wall with the wall having a plurality of ribs formed thereon, the ribs defining a channel extending therebetween, a plunger rod mountable within the housing and having at least one protrusion engageable within the channel, a cylindrical body, a spring mounted at a distal end of the housing with the spring being biased between the distal end and a needle hub, and a pusher rod raised such that pressure thereon from the plunger rod will cause the pusher rod to enter the cylindrical body, the pressure causing the spring to act on the needle hub to move the needle hub and the cylindrical body upwardly within the housing such that a needle is in an enclosed position within the housing and cannot be reused.

10 Claims, 6 Drawing Sheets

(58) Field of Classification Search
CPC .... A61M 5/3234; A61M 5/50; A61M 5/5013; A61M 5/502; A61M 2005/31508
See application file for complete search history.

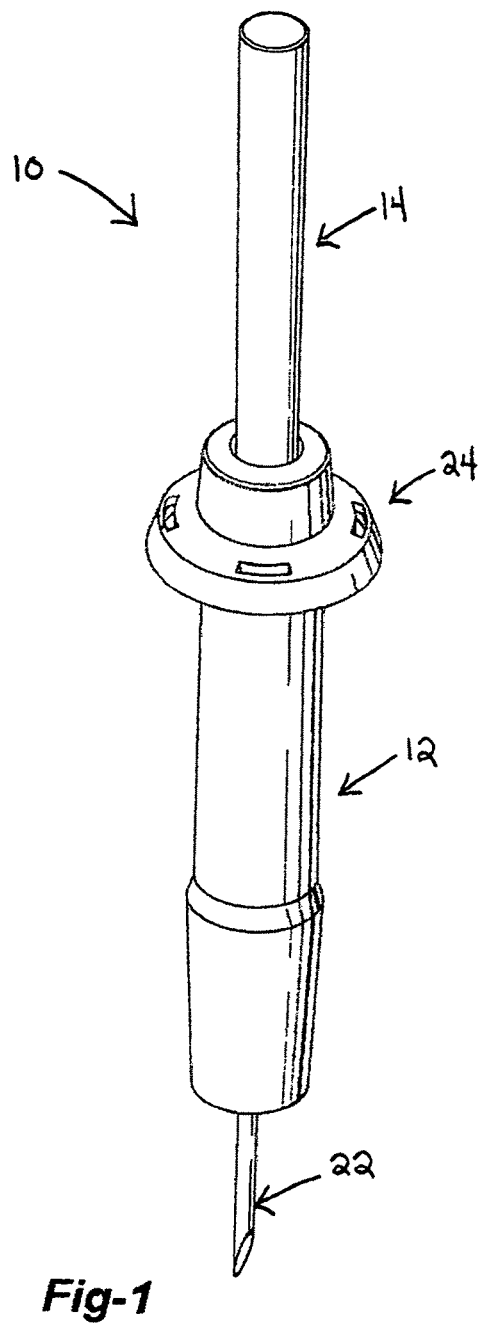
*Fig-1*
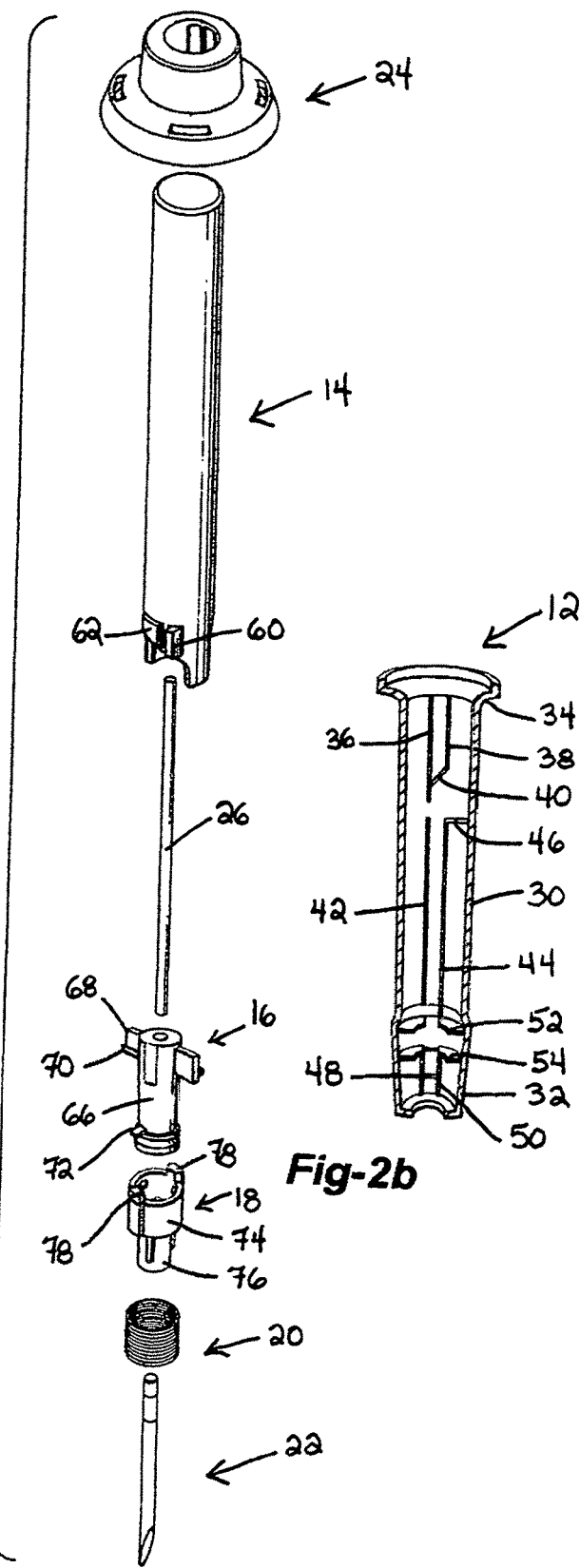
*Fig-2a*  *Fig-2b*

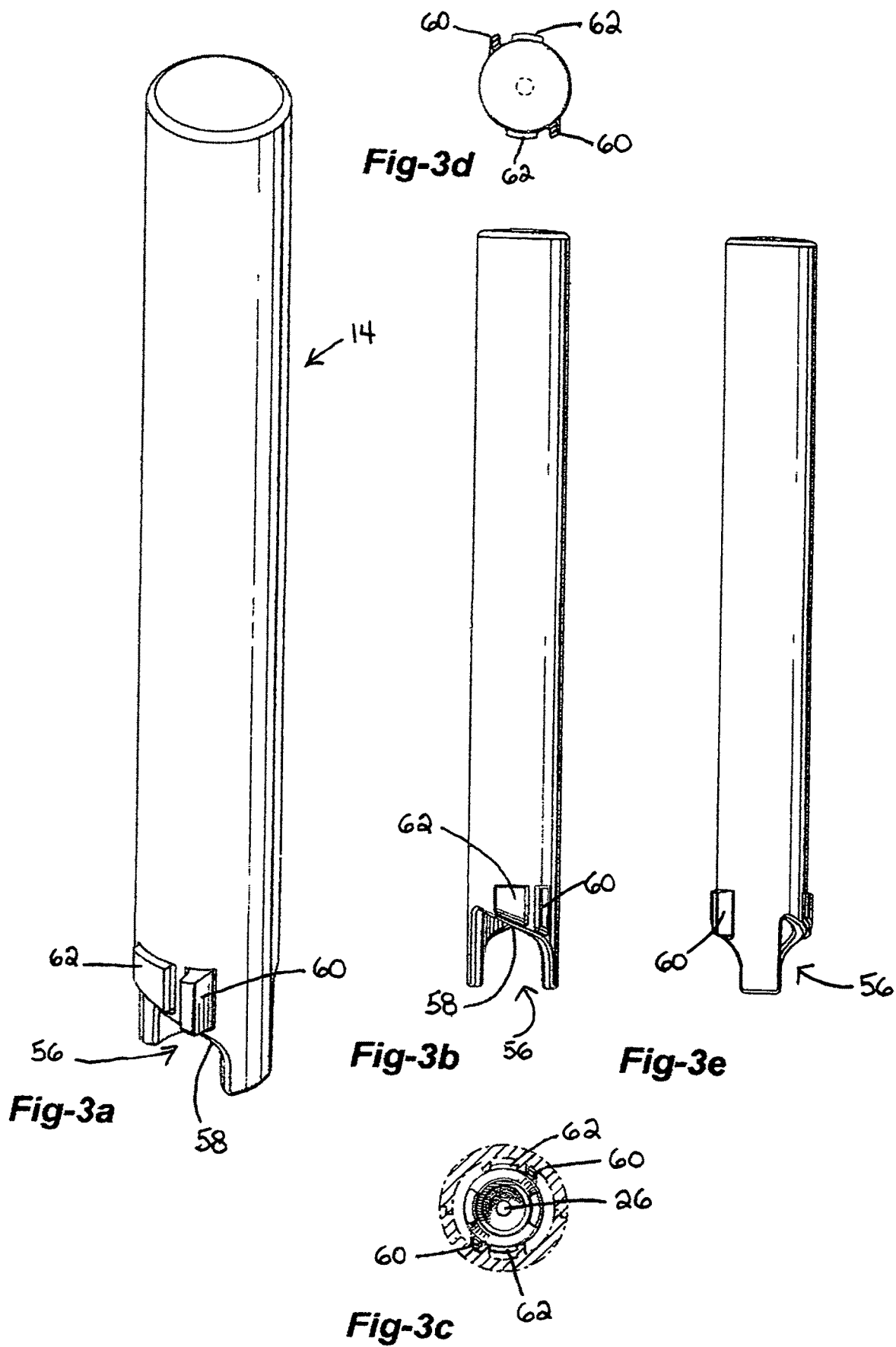

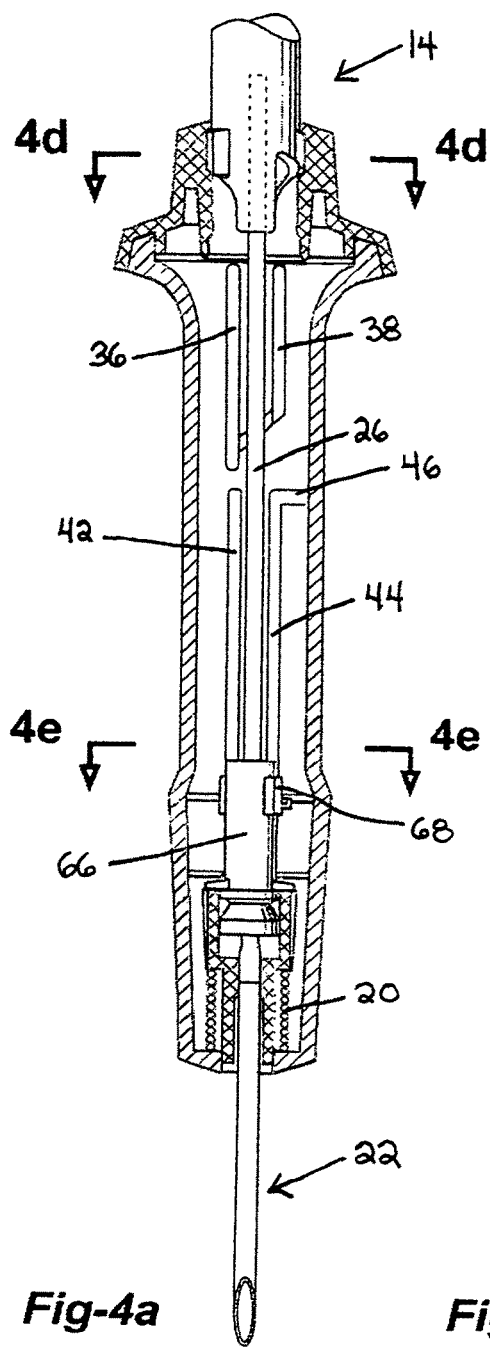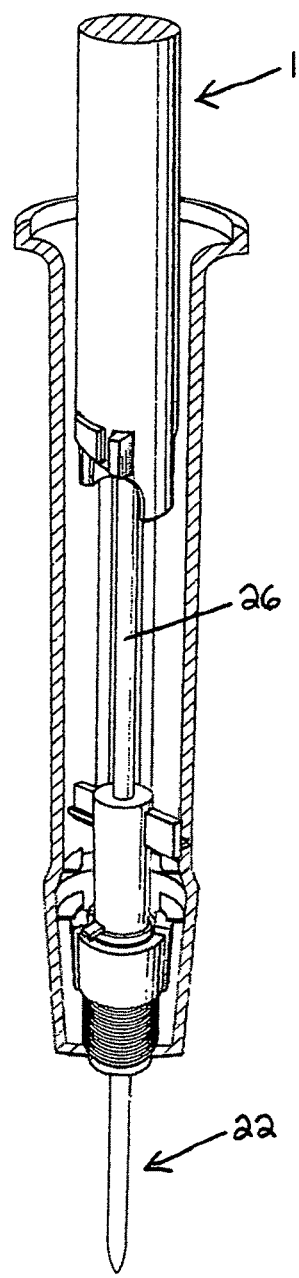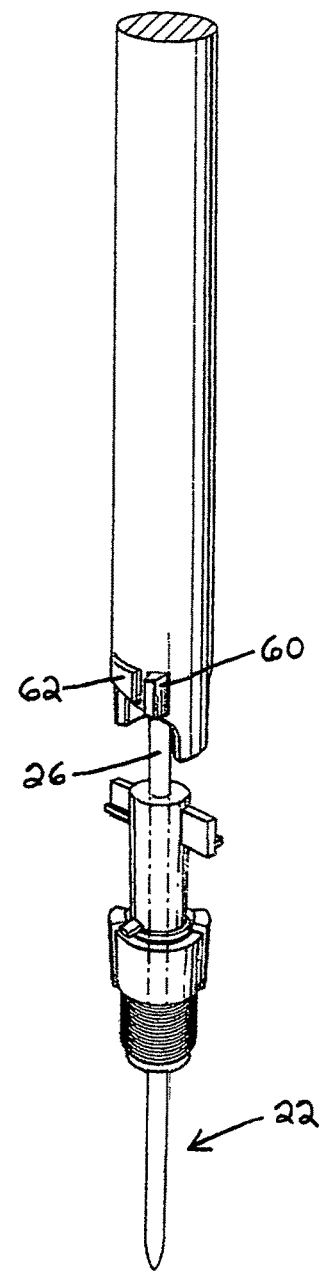
*Fig-4a*  *Fig-4b*  *Fig-4c*
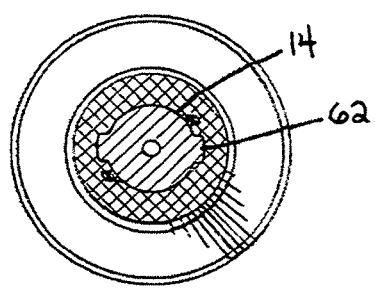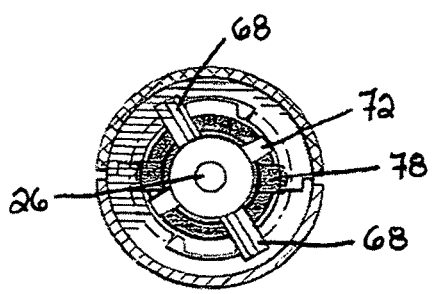
*Fig-4d*  *Fig-4e*

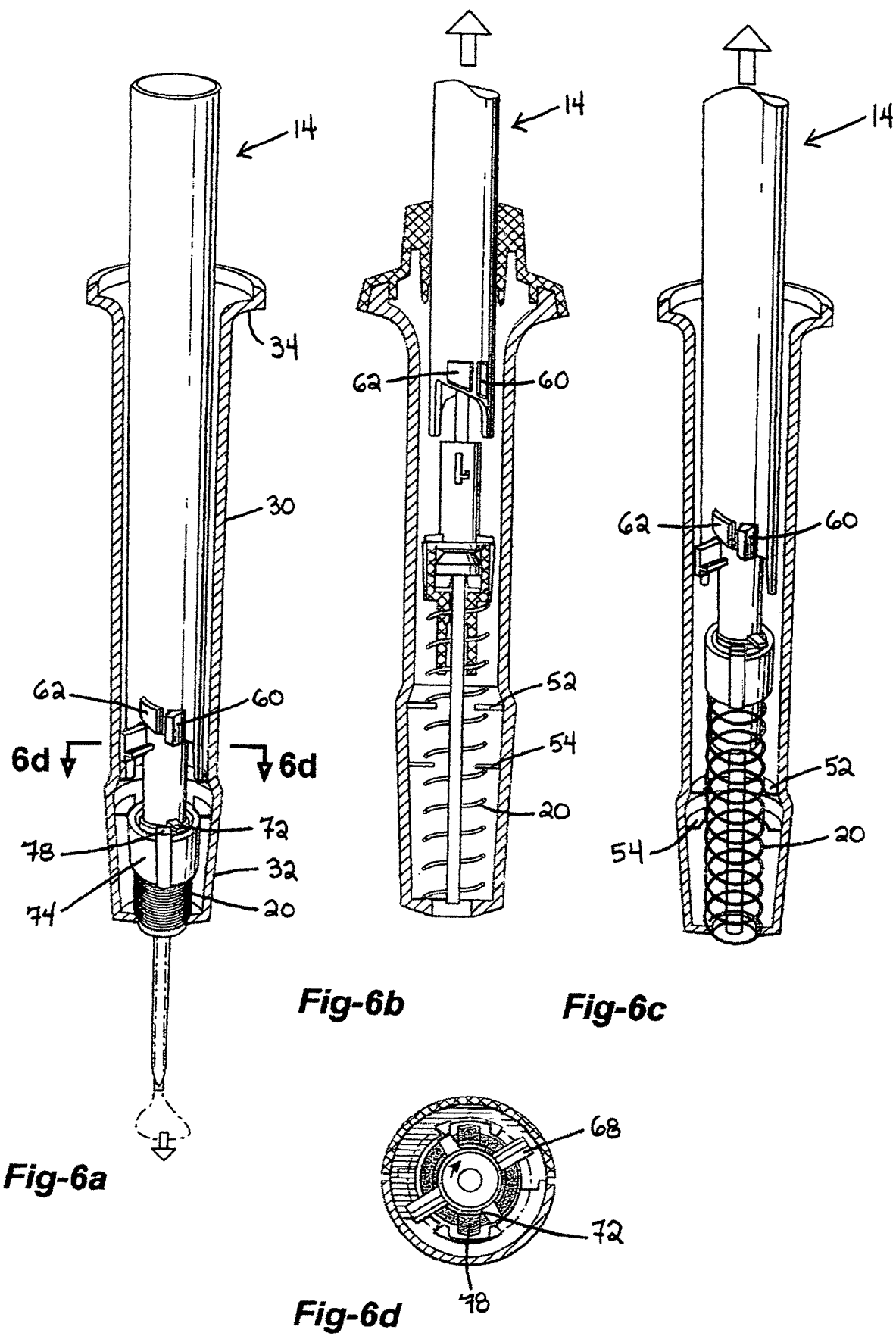

INJECTION DEVICE

CROSS-REFERENCE TO RELATED APPLICATIONS

This application is a 371 of PCT/CA2018/000124, filed Jun. 19, 2018, and foreign priority to CA 2,971,263, filed Jun. 19, 2017.

FIELD OF THE INVENTION

The present invention relates to an injection device and more particularly, relates to an injection device designed to dispense a drug for treating a mammal.

BACKGROUND OF THE INVENTION

Injection devices of various types are well known in the art. The purpose of the injection devices can vary including many injection devices which are designed to inject a liquid into a solid or semi-solid substrate. The present invention is particularly concerned with injection devices for injecting drugs into a mammal. Such injection devices are widely known and vary from simple syringes to complicated injection devices which may be designed to reach one or more end points.

SUMMARY OF THE INVENTION

According to the present invention, there is provided an injection device for injecting an injectable substance, said injection device comprising a housing, said housing having an interiorly facing wall, said wall having a plurality of ribs formed thereon, said ribs defining a channel extending therebetween, a plunger rod mountable within said housing, said plunger rod having at least one protrusion extending outwardly therefrom, a vial containing said injectable substance, said vial having at least one protrusion extending outwardly therefrom, a needle hub and a hollow needle secured thereto, a spring mounted at a distal end of said housing, said spring being biased between a distal end of said housing and said needle hub, and a pusher rod mounted within said plunger rod, said pusher rod being arranged such that pressure on said plunger rod will cause said pusher rod to push said injectable substance from said vial into said hollow needle for injection, said plunger rod having an arcuate surface at a proximal end thereof, said protrusion extending outwardly from said vial contacting said arcuate surface to cause rotation of said vial allowing said spring to move said vial upwardly within said housing.

As aforementioned, an injection device can be utilized for injecting a liquid into a mammal. In the instant application, a preferred material is a solid or semi-solid drug which is stored in a vial forming a portion of the injection device.

Preferably, the injection device of the present invention is packaged as a ready-to-use item with the needle already attached to a needle hub so that the device may be removed from the packaging and utilized "as is" to inject a patient who needs to be treated with the drug. Following the injection, the needle and associate components are withdrawn within a housing such that needle sticks and the like cannot occur. The device is designed to be of a single use type and the structure of the device prevents reuse of the same.

As used herein, the term "distal end" means an end which is used to inject the—i.e. the needle end, and the term "proximal end" refers to that end which is gripped by the person administrating the injection.

As set forth above, the injection device of the present invention can be used for injecting any injectable substance. The injectable substance may be in the form of a drug for treating a mammal, but the device of the present invention could equally well be utilized for other purposes. In a preferred embodiment, the device injects a substance into a mammal. In a particularly preferred embodiment, the injectable substance is in a solid or semi-solid state.

The device will include a housing which has an interiorly facing wall and a plunger rod which is movable within the housing. The plunger rod will move in a predetermined path which will be determined by ribs forming one or more channels within which the ribs ride.

The ribs are preferably performed during a molding operation as the housing is preferably formed of a plastic material. The ribs will have a width therebetween which defines the channels in which protrusions on a plunger rod move. It will be understood that in a preferred embodiment, the components of the invention are designed to be two-faced—i.e. each side of the housing will have its channel arrangement defined such that each side of the housing directs the internal components to be driven in the same given direction.

The invention will include a plunger rod which has one or more protrusions thereon which are designed to ride in the channels described above.

The device also includes a vial containing the injectable substance. The vial has the injectable substance driven in a given direction by a pusher rod which is associated with the plunger rod and which moves therewith. Located at the proximal end of the plunger rod is a needle hub which contains a needle for injection. Preferably, the vial sits on the needle hub and is rotatable with respect thereto. The rotatable movement is originally imparted to the vial through use of protrusions which contact an arcuate wall formed in the housing so as to impart a rotatable movement thereto. Due to this rotational movement, the needle hub and vial can be driven upwardly by means of a biased spring mounted within the housing. Naturally, this return movement occurs once the pusher rod has pushed the injectable substance into the needle and then into the patient or mammal.

After depletion of the injection, as above mentioned, the needle hub and vial are aligned with a channel in the housing such that the spring can act to drive the components (including the needle) within the housing wherein further use of the needle is prevented.

BRIEF DESCRIPTION OF THE DRAWINGS

Having thus generally described the invention, reference will be made to the accompanying drawings illustrating embodiments thereof, in which:

FIG. 1 is a perspective view of the assembled injection device;

FIG. 2a is an exploded view of the injection device;

FIG. 2b is a longitudinal sectional view of the housing;

FIG. 3a is a perspective view of the plunger rod;

FIG. 3b is side elevational view thereof as seen from the left hand side of FIG. 3a;

FIG. 3c is a bottom plan view thereof;

FIG. 3d is a top plan view thereof;

FIG. 3e is a perspective view as seen from the right hand side of FIG. 3A;

FIG. 4a is a longitudinal sectional view of the injection device is an assembled condition;

FIG. 4b is a perspective view of the longitudinal sectional view following commencing of activation;

FIG. 4c is a cutaway view illustrating activation of the device;

FIG. 4d is a sectional view taken along the lines 4D-4D of FIG. 4A;

FIG. 4e is a sectional view taken along the lines 4E-4E of FIG. 4A;

FIG. 6a is a perspective cutaway view of the device when injecting;

FIG. 6b is a longitudinal sectional view illustrating movement of the device subsequent to injection;

FIG. 6c is a perspective view thereof;

FIG. 6d is a sectional view taken along the lines 6D-6D of FIG. 6A; and

DETAILED DESCRIPTION OF THE INVENTION

Figure 5A:
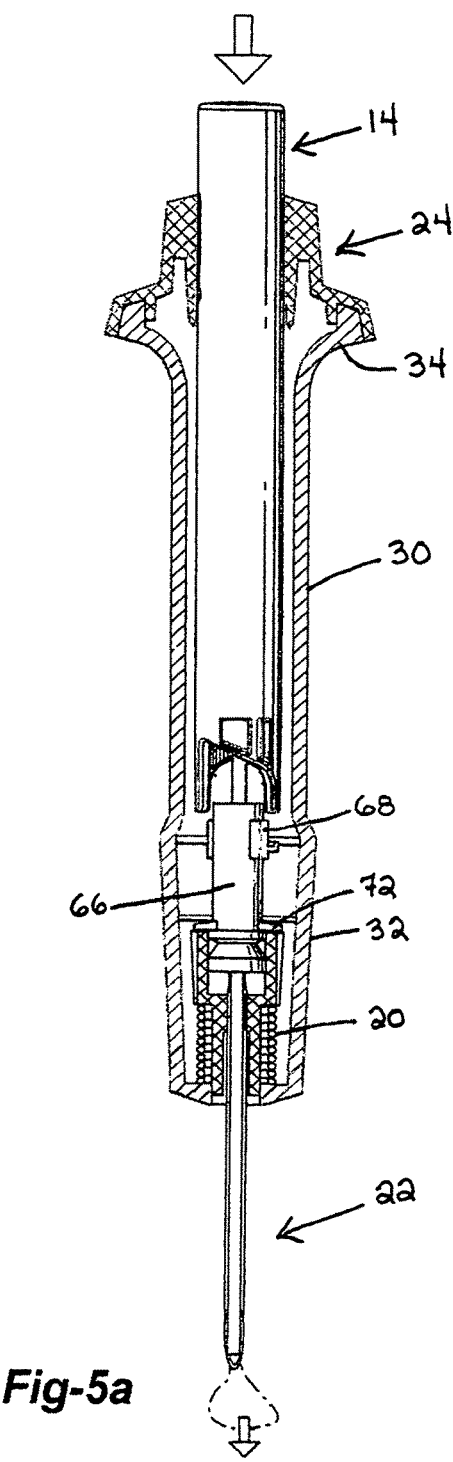
FIG. 5a is a sectional view illustrating injection of the injectable substance.
Figure 5B:
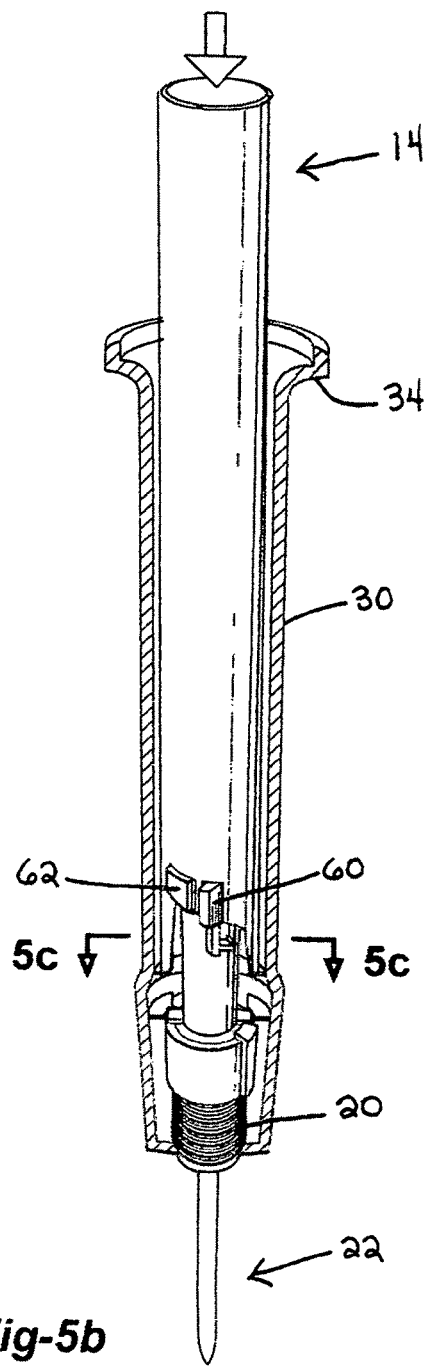
FIG. 5b is a cutaway perspective view thereof.
Figure 5C:
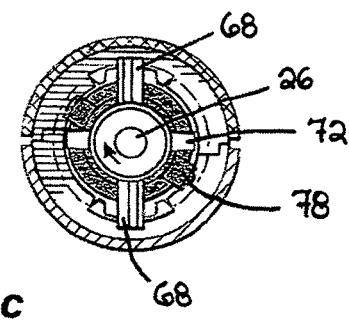
FIG. 5c is a sectional view taken along the lines 5C-5C of FIG. 5B.
Figure 7:
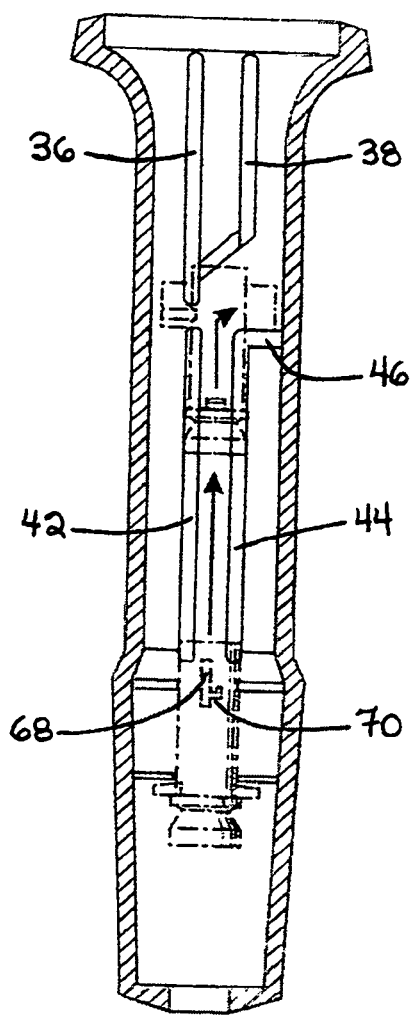
FIG. 7 is a cross-sectional view illustrating movement of the injection device after injection.

Referring to the drawings in greater detail and by reference characters thereto, there is illustrated in FIG. 1 an injection device generally designated by reference numeral 10. Injection device 10 has an outer enclosure 12 which surrounds the remaining components comprising a plunger rod generally designated by reference numeral 14, a vial generally designated by reference numeral 16, a needle hub 18, a spring 20, an injection needle 22, a cover 24 and a pusher rod 26.

As may be seen in FIG. 2b, housing 12 is formed of a main cylindrical side wall 30, a lower side wall 32 and an upper side wall portion 34. On the interior of cylindrical side wall 30, there is provided a first upper rib 36 and a second upper rib 38. A diagonal rib 40 extends between the end of second upper rib 38 and first upper rib 36.

A first lower rib 42 is parallel to a second lower rib 44. Extending outwardly from an upper end of second lower rib 44 is a horizontal rib 46.

Lower side wall 32 also has a lower rib 48 and a second lower rib 50 which is parallel thereto. This defines a channel therebetween. It is noted that there is a space between rib 42 and rib 48. As may be seen in FIG. 2b, the interior wall is also provided with an upper horizontal flange 52 and a lower horizontal flange 54.

Vial 16, as may be seen in FIG. 2a, includes a cylindrical body 66 having a pair of ears or upper protrusions 68 formed thereon. Each protrusion 68 has a somewhat L-shaped portion 70 located thereon. Vial 16 also includes lower protrusions 72 which extend outwardly from the body 66.

Needle hub 18, as seen in FIG. 2a, has an upper cylindrical body 74 and a lower cylindrical body 76. There are also provided upwardly extending protrusions 78 extending upwardly from upper cylindrical body 74. It will be noted that vial 16 sits on needle hub 18.

In operation, the injection device is assembled as illustrated in FIGS. 2a and 4a. It will be noted that raised portion 62 rides between ribs 36, 38, 42, 44 such that the plunger rod may be pushed downwardly such that pusher rod 26 will extend through vial 16 and push the medicament located downwardly into hollow needle 22. This may be accomplished during the motion wherein needle 22 is inserted into the patient.

In doing so, upper protrusions 68 contact recess arcuate wall 58 and are thus rotated due to the arcuate nature of recess wall 58. Ribs 48 and 50 prevent protrusions 78 from rotating. L-shaped portion 70 engages with the bottom of rib 42 to prevent upward movement. This rotation will bring upper protrusions 68 in line with the channel between ribs 42, 44. The pressure of spring 20 will then cause needle hub 18 and vial 16 to extend upwardly through housing 14. As the components are driven upwardly, protrusions 68 will contact diagonal rib 40 and thus go into the space between rib 38 and the wall. In doing so, further attempts to push on plunger rod 14 will be stopped by horizontal rib 46.

It will be understood that the above described embodiments are for purposes of illustration only and that changes and modifications may be made thereto without departing from the spirit and scope of the invention.

We claim:

1. An injection device for injecting an injectable substance, said injection device comprising:
 a housing, said housing having an interiorly facing wall, said wall having a plurality of parallel ribs formed thereon, said ribs defining a channel extending therebetween, wherein the plurality of parallel ribs comprises a first upper rib, a second upper rib, a first lower rib and a second lower rib;
 a diagonal rib extending between an end of the second upper rib and an end of the first upper rib;
 a horizontal rib extending radially from an upper end of said second lower rib;
 a plunger rod mountable within said housing, said plunger rod having at least one protrusion extending outwardly therefrom;
 a vial containing said injectable substance, said vial having at least one protrusion extending radially outwardly therefrom;
 a needle hub and a hollow needle secured thereto;
 a spring mounted at a distal end of said housing, said spring being biased between said distal end of said housing and said needle hub; and
 a pusher rod mounted within said plunger rod, said pusher rod being arranged such that depressing said plunger rod with a load will cause said pusher rod to push said injectable substance from said vial into said hollow needle for injection, said plunger rod having a recessed arcuate surface at a distal end thereof, said at least one protrusion extending radially outwardly from said vial contacting said recessed arcuate surface to cause rotation of said vial such that said at least one protrusion extending radially outward from said vial lines up with said channel allowing said spring to move said vial and said needle hub upwardly within said housing;
 wherein the at least one protrusion of said vial contacts said diagonal rib while said vial and said needle hub are driven upwardly within said housing by said spring, causing said at least one protrusion of the vial to move into a space between said second upper rib and said wall such that said horizontal rib prevents the plunger rod from being depressed again.

2. The injection device of claim 1 wherein said housing and said plunger rod have a circular pattern.

3. The injection device of claim 1 wherein said injectable substance is selected from a group consisting of a solid substance and a semi-solid substance.

4. The injection device of claim 1 wherein said needle hub has upwardly extending projections to stop the rotation of said vial at a desired point.

5. The injection device of claim 1 wherein said injection device is formed of a plastic material.

6. The injection device of claim 1 wherein a portion of said housing and said vial are formed of a transparent material such that said injectable substance is visually accessible.

7. The injection device of claim 1 wherein said at least one protrusion on said vial includes a generally L-shaped flange formed thereon.

8. An injection device for injecting, said injection device comprising:
- a housing having a plurality of parallel ribs formed on an interiorly facing wall of said housing, said ribs defining a channel extending therebetween, wherein the plurality of parallel ribs comprises a first upper rib, a second upper rib, a first lower rib and a second lower rib;
- a diagonal rib extending between an end of the second upper rib and an end of the first upper rib;
- a horizontal rib extending radially from an upper end of said second lower rib;
- a plunger rod mountable within said housing, said plunger rod having at least one protrusion extending outwardly therefrom;
- a cylindrical body having at least one protrusion extending radially outwardly therefrom;
- a needle hub and a hollow needle secured thereto;
- a spring mounted at a distal end of said housing, said spring being biased between said distal end of said housing and said needle hub; and
- said plunger rod having a recessed arcuate surface at a distal end thereof, said at least one protrusion extending radially outwardly from said cylindrical body contacting said recessed arcuate surface to cause rotation of said cylindrical body such that said at least one protrusion extending radially outward from said cylindrical body lines up with said channel allowing said spring to move said cylindrical body and said needle hub upwardly within said housing in response to said plunger rod being depressed;
- wherein said at least one protrusion of said cylindrical body contacts said diagonal rib while said cylindrical body and said needle hub are driven upwardly within said housing by said spring, causing said at least one protrusion of said cylindrical body to move into a space between said second upper rib and said wall such that said horizontal rib prevents the plunger rod from being depressed again.

9. The injection device of claim 8, further comprising a solid injectable substance disposed in the cylindrical body.

10. The injection device of claim 9, further comprising a pusher rod mounted within said plunger rod, said pusher rod being arranged such that a load on said plunger rod will cause said pusher rod to push said injectable substance from said cylindrical body into said hollow needle for injection.

\* \* \* \* \*